US011214262B2

(12) United States Patent
Salter et al.

(10) Patent No.: US 11,214,262 B2
(45) Date of Patent: Jan. 4, 2022

(54) VIRTUAL SOOTHING IN A TRANSPORTATION VEHICLE

(71) Applicant: Ford Global Technologies, LLC, Dearborn, MI (US)

(72) Inventors: Stuart Salter, Dearborn, MI (US); Pietro Buttolo, Dearborn, MI (US); Annette Huebner, Dearborn, MI (US); Paul Kenneth Dellock, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/960,987

(22) PCT Filed: Jan. 31, 2018

(86) PCT No.: PCT/US2018/016260
§ 371 (c)(1),
(2) Date: Jul. 9, 2020

(87) PCT Pub. No.: WO2019/152025
PCT Pub. Date: Aug. 8, 2019

(65) Prior Publication Data
US 2020/0353936 A1    Nov. 12, 2020

(51) Int. Cl.
*B60W 40/08* (2012.01)
*H04W 4/40* (2018.01)
(Continued)

(52) U.S. Cl.
CPC ......... *B60W 40/08* (2013.01); *A61B 5/02055* (2013.01); *G08B 21/0211* (2013.01);
(Continued)

(58) Field of Classification Search
CPC ......... B60W 40/08; B60W 2040/0827; B60W 2040/0872; B60W 2040/0881;
(Continued)

(56) References Cited

U.S. PATENT DOCUMENTS 5,802,314 A    9/1998    Tullis et al.
8,825,277 B2    9/2014    McClellan et al.
(Continued)

FOREIGN PATENT DOCUMENTS

WO    2017/089530 A1    6/2017

OTHER PUBLICATIONS

International Search Report of the International Searching Authority for PCT/US2018/016260 dated Apr. 13, 2018.

*Primary Examiner* — Van T Trieu
(74) *Attorney, Agent, or Firm* — Brandon Hicks; Eversheds Sutherland (US) LLP

(57) ABSTRACT

Virtual soothing in a transportation vehicle is described, in which soothing a passenger in a vehicle may involve receiving monitoring data relevant to the passenger from a plurality of sensors in the vehicle, determining a soothing need or an emergency condition of the passenger based on the monitoring data, and presenting a multimedia message to the passenger that addresses the soothing need or the emergency condition. The multimedia message may be specific to the passenger and relevant to the soothing need or the emergency condition. The multimedia message may exhibit characteristics that enable the passenger to perceive the multimedia message as being verbally generated by a guardian with whom the passenger is personally acquainted.

20 Claims, 4 Drawing Sheets

(51) Int. Cl.
*A61B 5/0205* (2006.01)
*G08B 21/02* (2006.01)
*H04W 4/90* (2018.01)
*B60W 60/00* (2020.01)
*A61B 5/00* (2006.01)
*H04L 12/58* (2006.01)

(52) U.S. Cl.
CPC .......... *G08B 21/0277* (2013.01); *H04W 4/40* (2018.02); *A61B 5/6893* (2013.01); *B60W 60/0016* (2020.02); *B60W 2540/221* (2020.02); *H04L 51/04* (2013.01); *H04W 4/90* (2018.02)

(58) Field of Classification Search
CPC ...... B60W 60/00; B60R 16/02; B60R 16/037; G08B 21/00; G08B 21/02; G08B 21/0211; G08B 21/0277; G08B 25/016; A61B 5/0002; A61B 5/021; A61B 5/18
See application file for complete search history.

(56) References Cited

U.S. PATENT DOCUMENTS

| | | | |
|---|---|---|---|
| 9,736,688 B2 * | 8/2017 | Li | H04L 67/1097 |
| 10,268,530 B2 * | 4/2019 | Breaux | H04W 4/33 |
| 2005/0080533 A1 | 4/2005 | Basir et al. | |
| 2005/0274561 A1 | 12/2005 | Claar et al. | |
| 2014/0309864 A1 * | 10/2014 | Ricci | G01C 21/365 |
| | | | 701/36 |
| 2014/0364751 A1 | 12/2014 | Dugan et al. | |
| 2016/0052391 A1 | 2/2016 | Walsh et al. | |
| 2017/0151959 A1 | 6/2017 | Boesen | |
| 2019/0047498 A1 * | 2/2019 | Alcaidinho | G06F 3/14 |

\* cited by examiner

VIRTUAL SOOTHING IN A TRANSPORTATION VEHICLE

TECHNICAL FIELD

The present disclosure generally relates to automotive vehicles and, more particularly, to virtually soothing a passenger being transported in a manned or unmanned transportation vehicle.

BACKGROUND

Some passengers of an automotive transportation vehicle (e.g., a car, a min-van, or a bus; hereinafter referred as "a vehicle") may not be suitable to travel alone in the vehicle, due to health or age for example, regardless whether the vehicle is autonomous or human-operated. For the benefit of such passengers, at least for safety concerns, these passengers may preferably be accompanied by a caregiver or a guardian during the trip. As an example, a passenger may be a child having epilepsy or seizure disorders, and thus can possibly have a seizure during the trip. As another example, a passenger may be an elderly person suffering from Alzheimer's disease or dementia. The passenger may have instances of memory loss and/or time/space disorders during the trip. For instance, the patient may forget why he or she is in the vehicle and what the destination is for the trip, and thus may start to feel uneasy or disoriented while sitting in the vehicle.

In either of the examples above, the passenger would likely become increasingly panic or distressed, or even medically in danger, without a caregiver or a guardian (e.g., a parent, a family member, a friend, a nurse or a family doctor; hereinafter referred as "a guardian") of the passenger in the vehicle to soothe, assure or otherwise calm the patient in a timely manner. Therefore, it typically requires a guardian to accompany such a passenger in a vehicle during the entirety of a trip. As memory loss or seizure may occur at any time for the passenger, a guardian is necessary regardless the length of the trip. In other words, in cases where a guardian is not readily available to travel with the passenger, the mobility of the passenger to go on a road trip, even a local one, is greatly limited. Consequently, the quality of life of such passengers may be negatively impacted significantly.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

In the following description, reference is made to the accompanying drawings that form a part thereof, and in which is shown by way of illustrating specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

As described above, there may be safety concerns, among others, for a passenger having special needs (e.g., a child having epilepsy or an elderly person having Alzheimer's disease) to ride a transportation vehicle by himself or herself without being accompanied by a guardian. Thus, a passenger having special needs may not be able to go on a trip in a vehicle unless a guardian is readily available to go with the passenger. The present disclosure provides methods and apparatuses that enable or otherwise enhance the feasibility of such a passenger going on a trip in a vehicle without a guardian's company. The vehicle may have an intelligence to monitor the situation of the passenger during the trip. The vehicle may also soothe the passenger using various means during the trip, along with direct or indirect help from a guardian who is located elsewhere (i.e., not being physically located in the vehicle) during the trip. The vehicle may further initiate a suggested or mandatory route change in an event that an emergency condition of the passenger exists.

Figure 1:
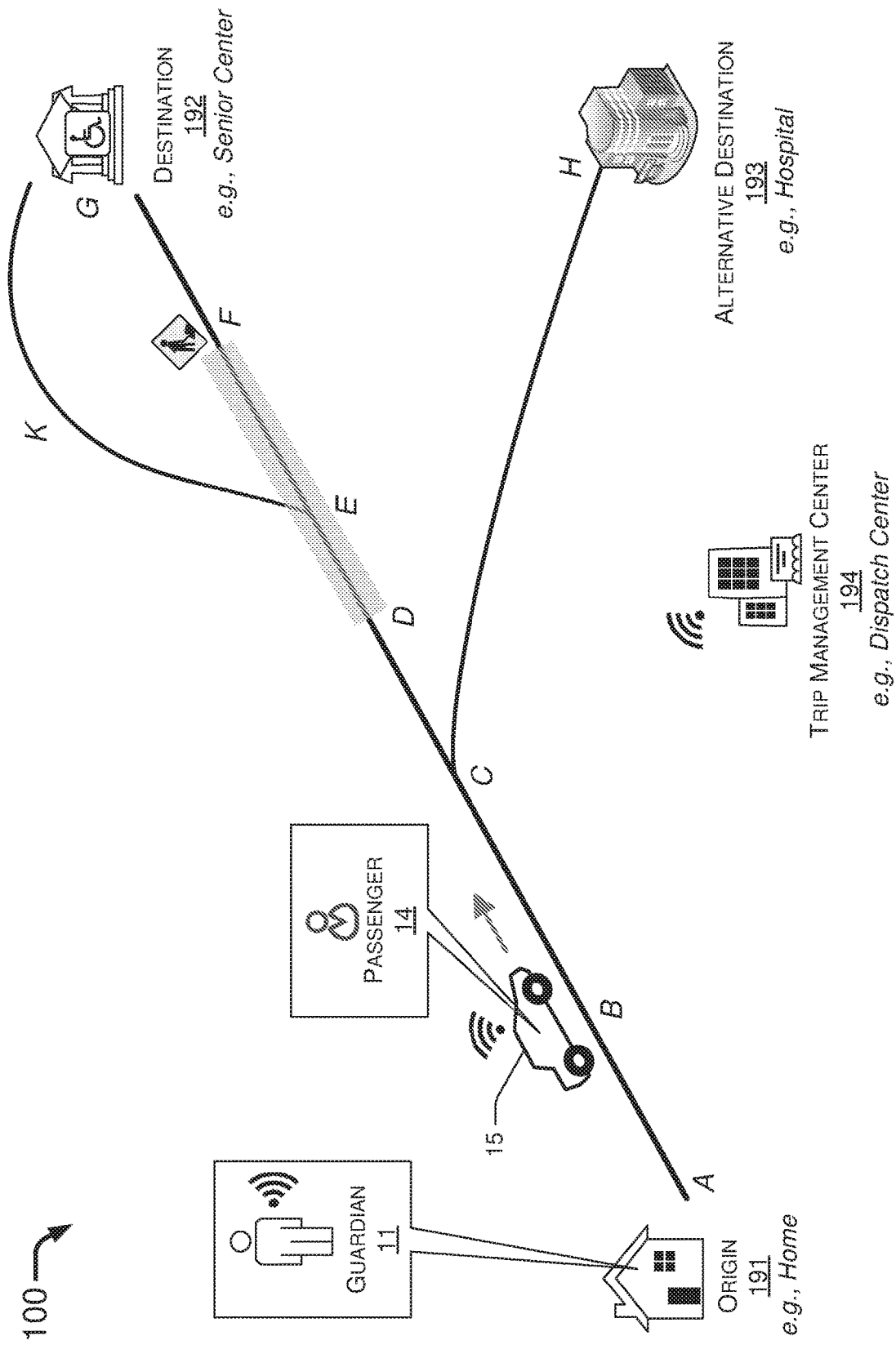
FIG. 1 is a diagram depicting an example scenario in which embodiments in accordance with the present disclosure may be utilized.

Various embodiments described in the present disclosure may be applied to an example scenario 100 depicted in FIG. 1. Scenario 100 may include a transportation vehicle 15 transporting a passenger 14 for whom the presence of a guardian is desirable (e.g., passenger 14 may suffer from epilepsy and/or Alzheimer's disease). A trip may entail a plan for vehicle 15 to transport passenger 14 from an origin 191 (e.g., home of passenger 14) located at point A of FIG. 1 to a destination 192 (e.g., a senior center) located at point G of FIG. 1. Specifically, vehicle 15 may be intended by a guardian 11 of passenger 14 to transport passenger 14 from home 191 to senior center 192 via a predetermined route along points A-B-C-D-E-F-G as shown in FIG. 1. That is, the predetermined route between home 191 and senior center 192 along points A-B-C-D-E-F-G may have been approved by guardian 11 for the trip.

Passenger 14 may be personally acquainted with guardian 11. Guardian 11 may have sufficient knowledge regarding the trip and passenger 14, and may have an authority to approve a route change for the trip for the benefit of passenger 14, including canceling the trip if deemed necessary. Guardian 11 may be, for example, a family member, a caregiver, a friend or a neighbor of passenger 14. Alternatively, guardian 11 may be a nurse or a doctor who has been taking care of passenger 14. Guardian 11 does not accompany passenger 14 within vehicle 15 during the trip. For instance, guardian 11 may be a family member of passenger 11, and stays at home 191, as illustrated in FIG. 1, while vehicle 15 transports passenger 14 to senior center 192 along the predetermined route. Alternatively, guardian 11 may be a doctor of passenger 11, and is working at hospital 193 when passenger 14 is on the trip from home 191 to senior center 192.

During the trip, vehicle 15 may monitor physiological conditions of passenger 14, as well as how passenger 14 interacts with vehicle 15. In particular, vehicle 15 may be equipped with a plurality of monitoring sensors, which may generate monitoring data that is relevant to passenger 14 during the trip. More details of the monitoring sensors will be provided at a later part of the present application. Vehicle 15 may have a processor that is capable of collecting or otherwise receiving the monitoring data from the monitoring sensors. The processor may further determine whether passenger 14 may have a soothing need or even an emergency condition during the trip. Once the processor of vehicle 15 determines that passenger 14 has a soothing need (e.g., passenger 14 appears panic because the passenger forgets where vehicle 15 is taking him or her), the processor may take a series of escalating measures as an effort to address the soothing need and to calm down passenger 14. In an event that the processor determines passenger 14 is having an emergency condition (e.g., passenger 14 appears losing consciousness or having a seizure), the processor may initiate a suggested or mandatory route change such that the trip is changed and vehicle 15 drives to an alternative destination, such as hospital 193 as shown in FIG. 1.

The sensors with which vehicle 15 of FIG. 1 is equipped may include sensors in two major categories: physiological sensors and user-interface sensors. The physiological sensors may be capable of monitoring various vital signs of passenger 14, whereas the user-interface sensors may be capable of monitoring interactions between passenger 14 and vehicle 15 during the trip. The physiological sensors may include, for example and not limited to, a respiration sensor, a pulse senor, a blood pressure sensor and a thermometer for measuring and monitoring a respiration rate, a pulse rate, blood pressure readings and a body temperature of passenger 14, respectively. The physiological sensors may be installed at locations within vehicle 15 that are convenient for achieving the measuring and monitoring purpose. For instance, the physiological sensors may be embedded on, in or close to the armrest, back or seatbelt of one or more of the seats of vehicle 15. When passenger 14 is seated in a seat of vehicle 15, the processor may receive from the physiological sensors vital sign readings of passenger 14 as monitoring data. In addition, the physiological sensors may include wearable monitors that are worn by passenger 14. The processor of vehicle 15 may also receive monitoring data from the wearable monitors. The wearable monitors may also provide to the processor vital sign data such as blood pressure, pulse rate, respiration rate and/or body temperature of passenger 14. The wearable monitors may also track limb movement of passenger 14, which may become unusually intense in an event that passenger 14 is having a seizure.

Figure 2:
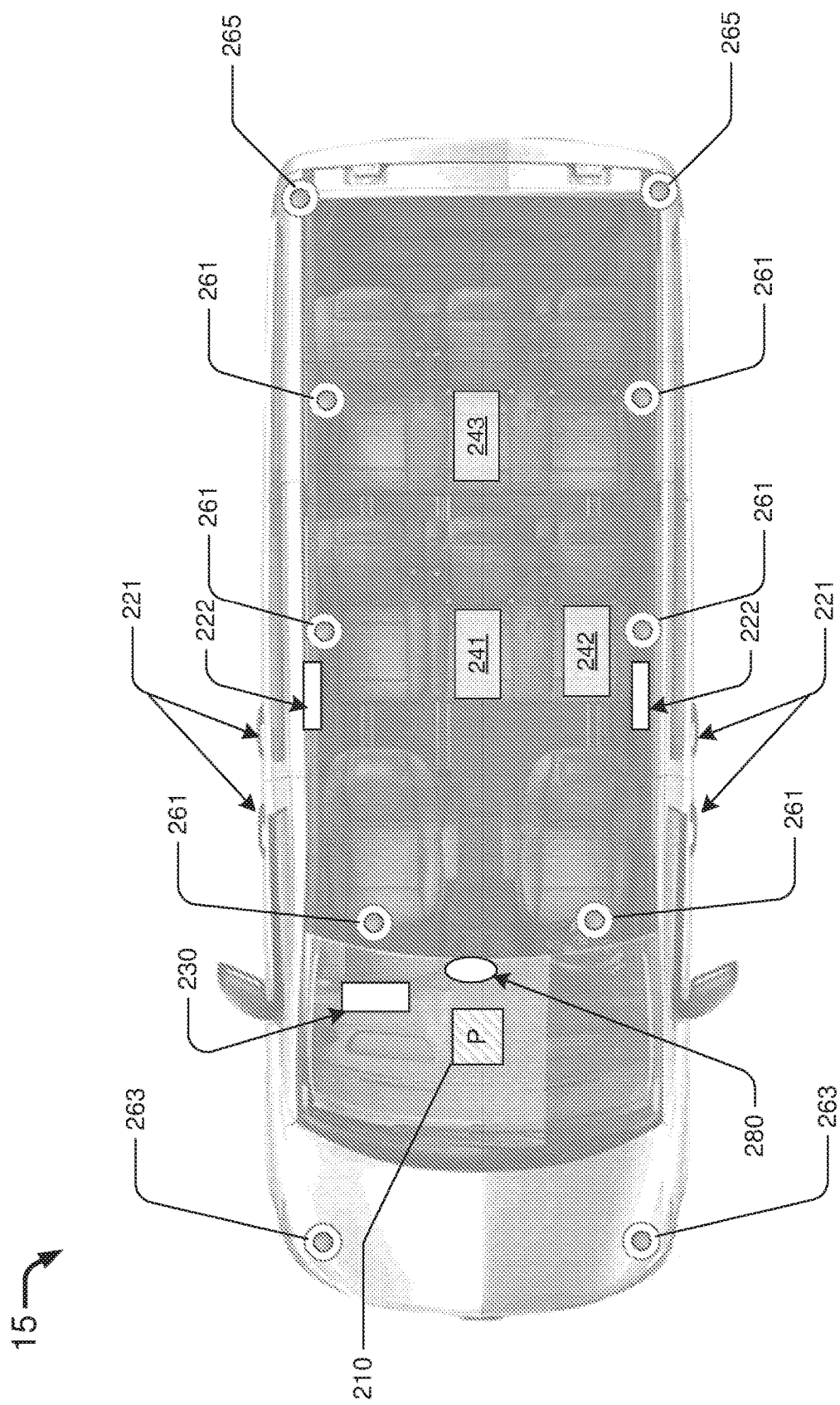
FIG. 2 is a diagram showing vehicle sensors which embodiments in accordance with the present disclosure may utilize.

On the other hand, the user-interface sensors of vehicle 15 may be capable of monitoring interactions between passenger 14 and vehicle 15 during the trip. FIG. 2 illustrates a few example user-interface sensors of vehicle 15 of FIG. 1. As shown in FIG. 2, vehicle 15 may have a wide-angle video camera 280 that is capable of monitoring in-vehicle behavior of passenger 14. Vehicle 15 may also have a high-sensitivity microphone (not shown in FIG. 2) that is capable of monitoring in-vehicle sounds or dialogues, including murmur or self-talk of passenger 14. The processor of vehicle 15, such as processor 210 shown in FIG. 2, may receive audio and/or video data captured by the high-sensitivity microphone and/or wide-angle video camera 280 as monitoring data relevant to passenger 14. In some embodiments, the user-interface sensors of vehicle 15 may include external door handles 221 and internal door handles 222 of FIG. 2. Each of external door handles 221 and internal door handles 222 may be of capacitive type and thus able to send a signal as monitoring data to processor 210 when being touched by a human, including passenger 14. In some embodiments, the user-interface sensors of vehicle 15 may include seat-occupation sensors, such as seat-occupation sensors 241, 242 and 243 shown in FIG. 2. Each of seat-occupation sensors 241, 242 and 243 may send a signal as monitoring data to processor 210 indicating whether a respective seat is being occupied or not. In some embodiments, the user-interface sensors of vehicle 15 may include seatbelt-buckling switches (not shown in FIG. 2) each associated with a seatbelt of vehicle 15. Each of the seatbelt-buckling switches may send a signal as monitoring data to processor 210 indicating whether a respective seatbelt is bucked or not. In some embodiments, the user-interface sensors of vehicle 15 may include window switches (not shown in FIG. 2) each associated with a window of vehicle 15. Each of the window switches may send a signal as monitoring data to processor 210 indicating whether a window glass pane of a respective window is being actuated (i.e., moved up or down) or not. In some embodiments, the user-interface sensors of vehicle 15 may include a Bluetooth Low Energy (BLE) in-vehicle positioning system (hereinafter referred as "a BLE locator") that is capable of locating the whereabout of passenger 14 within vehicle 15 using BLE triangulation techniques. The BLE locator may include a BLE tag worn by passenger 14 (e.g., a cell phone carried by passenger 14), as well as a network of BLE antennas each disposed at a different location within vehicle 15. As shown in FIG. 2, the network of BLE antennas may include six BLE antennas 261 each disposed close to an interior light of vehicle 15, two BLE antennas 263 each disposed close to a headlight of vehicle 15, and two BLE antennas 265 each disposed close to a tail light of vehicle 15. Based on the received strengths at the BLE antennas of a BLE signal originated from the BLE tag, a location of passenger 14 within vehicle 15 may be determined. Processor 210 may receive the location of passenger 14 as monitoring data.

Based on the monitoring data received from the physiological sensors and/or the user-interface sensors, processor 210 of vehicle 15 may determine one or more soothing needs and/or emergency conditions of passenger 14. For example, processor 210 may include a cascaded neural network (CNN) that is capable of analyzing video data (e.g., a video footage of passenger 14) as captured by wide-angle video camera 280. The CNN may classify or otherwise interpret the video data as showing passenger 14 in an emergency condition. For example, the CNN may analyze the video data and interpret that passenger 14 is having a seizure. Processor 210 may subsequently determine the seizure as an emergency condition of passenger 14. As another example, based on monitoring data received from the seat-occupation sensors, the seatbelt-buckling switches and the BLE locator, processor 210 may determine that passenger 14 has disengaged the seatbelt and appears to be moving about different seats within vehicle 15 while vehicle 15 is in transit, and subsequently determine that passenger 14 is having a soothing need (i.e., passenger 14 needs to be calmed down and stay in a seat). Similarly, as another example, based on monitoring data received from internal door handles 222, processor 210 may find that passenger 14 is repeatedly trying to open a door of vehicle 15 while vehicle 15 is in transit, and determine that passenger 14 is having a soothing need. Alternatively, the high-sensitivity microphone of vehicle 15 may capture passenger 14 repeatedly murmuring "I want to go home. I want to go home.", which is sent to processor 210 as monitoring data. Based on the monitoring data received from the high-sensitivity microphone, processor 210 may thus determine that passenger 14 is having a soothing need. As still another example, based on the vital sign readings received from the physiological sensors, processor 210 may find that the blood pressure readings of passenger 14 may be at a medically dangerous low level, and thus determine that passenger 14 may be in an emergency condition. In some embodiments, processor 210 may keep guardian 11 posted about the soothing need or the emergency condition as determined by processor 210.

After determining a soothing need or an emergency condition of passenger 14 as described above, processor 210 may proceed to determine whether a suggested or mandatory route change may be required. For example, processor 210 may determine, when vehicle 15 is around point B of the predetermined route (as shown in FIG. 1), that passenger 14 is in an emergency condition and requires immediate medical attention. Processor 210 may then determine that a route change is needed. Specifically, processor 210 may determine that vehicle 15 needs to take an alternative route (e.g., route A-B-C-H of FIG. 1) and transport passenger 14 to an alternative destination (e.g., hospital 193 of FIG. 1). In some embodiments, especially when the route change is deemed mandatory, processor 210 may control vehicle 15 to head to alternative destination 193 prior to, or even without, obtaining an approval of the route change from guardian 11. Processor 210 may notify guardian 11 about the route change by sending a text message or an email to guardian 11, but the approval of the route change may not be needed to necessitate the route change. In some embodiments, especially when the route change is only suggested but not mandatory, processor 210 may try to obtain an approval of the route change from guardian 11 prior to changing the route and driving vehicle 15 toward alternative destination 193. That is, processor 210 may send guardian 11 a route change request (i.e., a request for route change) requesting an approval of the route change, but would not actually transport passenger 14 to alternative destination 193 via the alternative route until processor 210 receives the approval of the route change from guardian 11. In some embodiments, processor may announce the route change to passenger 14 either audibly or visually through a speaker or a visual display in vehicle 15. In some embodiments, processor 210 may establish a communication link between vehicle 15 and guardian 11 via a communication circuit of vehicle 15. Guardian 11 may announce the route change to passenger 14 through the communication link. A voice of guardian 11 announcing the route change may soothe passenger 14 and alleviate a soothing need or an emergency condition passenger 14 is having.

In some embodiments, a route change may also be triggered by a condition of excess or slow traffic. Use scenario 100 as an example. A road work at point F of the predetermined route may have caused traffic to slow down between point D and F along the predetermined route, and vehicle 15 may start to experience the slower traffic after passing point D. Processor 210 of vehicle 15 may thus determine a suggested route change which takes an alternative route D-E-K-G to arrive at destination 192, instead of the predetermined route D-E-F-G, so as to avoid much of the slow traffic. Alternatively, vehicle 15 may receive traffic information before even experiencing the slow traffic and then decide to make a route change. For example, vehicle 15 may receive, when vehicle 15 just leaving origin 191, traffic information regarding the slow traffic between point D and point F. Processor 210 may then determine to take an alternative route A-B-C-D-E-K-G, instead of the predetermined route A-B-C-D-E-F-G, even before vehicle 15 experiences the slow traffic between point D and E along the route.

In some embodiments, processor 210 may also notify a base station or a dispatch center (e.g., trip management center 194 of FIG. 1) about the route change, regardless if the route change is mandatory or suggested.

In an event that processor 210 determines that passenger 14 is having a soothing need, processor 210 may take a series of escalating measures as an effort to address the soothing need and calm down passenger 14. For example, processor 210 may determine that passenger 14 is having a soothing need after receiving monitoring data from a seatbelt-buckling switch indicating that passenger 14 has disengaged his or her seatbelt buckle. To address the soothing need of passenger 14, processor 210 of vehicle 15 may present a multimedia message to passenger 14 that is relevant to the soothing need. The multimedia message may be an audio message or a video message, or a combination of both. For instance, processor 210 may broadcast through a speaker in vehicle 15 an audio message stating "Please buckle your seatbelt." Alternatively, processor 210 may show on a video display of vehicle 15 a video clip containing the same message. In some embodiments, the multimedia message may be pre-recorded by a guardian of passenger 14 prior to the trip, or at least prior to the determining of the soothing need by processor 210 during the trip. For instance, vehicle 15 may receive a multimedia message verbally generated by a doctor of passenger 14 who is working at hospital 193, and save the multimedia message in a memory in vehicle 15. Also for instance, the multimedia message may be verbally generated by guardian 11 at home 191 and saved in the memory before vehicle 15 starts the trip at point A. Since the multimedia message is pre-recorded by guardian 11, the multimedia message may exhibit characteristics that may enable passenger 14 to recognize or otherwise perceive the multimedia message as being verbally generated by guardian 11 when presented with the soothing message in vehicle 15. In some embodiments, guardian 11 may not need to pre-record the multimedia soothing message. That is, processor 210 may include a multimedia synthesizer that is capable of synthesizing or otherwise generating the multimedia message using various audio-synthesis or video-synthesis techniques. The multimedia message may be synthesized such that it exhibits characteristics of guardian 11. When the multimedia message is presented to passenger 14, the characteristics of the synthesized multimedia message would enable passenger 14 to perceive the multimedia message as being verbally generated by guardian 11. The multimedia message would be more effective in addressing the soothing need of passenger 14 if passenger 14 perceives the multimedia message as being verbally generated by someone he or she is acquainted with, such as guardian 11 or the doctor. The multimedia synthesizer may access a characteristics database specific to guardian 11 and a message content database specific to passenger 14. The characteristics database may store parameters representing various sound and facial characteristics of guardian 11. The message content database may store message contents that are useful in soothing passenger 14. Both the characteristics database and the message content database may be downloaded or otherwise stored in the memory of vehicle 15.

In some embodiments, the multimedia message may be specific to passenger 14 so as to be more effective in addressing the soothing need and soothe passenger 14. Namely, the multimedia message may be tailored, customized or personalized for the audience, in this case, passenger 14, whose name is "Johnny". For example, a soothing multimedia message may explicitly call out the name of passenger 14. That is, instead of a neutral or template multimedia message stating "Please buckle your seatbelt.", the multimedia message may be recorded or synthesized to be specific to passenger 14 by stating: "Johnny, would you buckle up your seatbelt for me?". After passenger Johnny complies by having his seatbelt buckled up, another soothing message may follow to confirm him, such as: "Well done, Johnny! I am so proud of you!". Apparently, personalized soothing messages like these will be much more effective in soothing the passenger than impersonal template messages.

After presenting the soothing message to passenger 14, processor 210 of vehicle 15 may continue receiving monitoring data relevant to passenger 14 from the physiological sensors and user-interface sensors, and determine if the soothing need has been addressed and fulfilled successfully. In an event that the soothing need of passenger 14 persists, processor 210 may escalate the soothing measures. For example, processor 210 may contact guardian 11 and notify him or her of the soothing need of passenger 14. In some embodiments, processor 210 may call or otherwise notify guardian 11 about the soothing need via a text massage or an email. In some embodiments, processor 210 may also include the monitoring data in the text message or email so that guardian 11 has more detailed information regarding the soothing need or emergency condition of passenger 14. In some embodiments, processor 210 may further establish a one-way communication link from vehicle 15 to guardian 11. Guardian 11 may then monitor, in a real-time manner, passenger 14 during the trip via the one-way communication link. In some embodiments, processor 210 may establish a two-way communication link between vehicle 15 and guardian 11. Guardian 11 and passenger 14 may then use the two-way communication link to communicate with one another in a real-time manner, and guardian 11 may be able to directly address the soothing need over the two-way communication link. If the soothing need still persists (e.g., guardian 11 is not available to answer the call from vehicle 15 at the moment), processor 210 of vehicle may further escalate the soothing measures. For example, processor 210 may contact a base station or trip management center (e.g., dispatch center 194 of FIG. 1) or a hospital (e.g., hospital 193 of FIG. 1) for intervention. Professionally trained personnel at the base station or the hospital may be able to address the soothing need of passenger 14 through a two-way communication link between vehicle 15 and the base station or the hospital. In some embodiments, processor 210 of vehicle 15 may escalate the soothing measures and establish a 3-way communication between guardian 11, passenger 14 and the base station or the hospital to address the soothing need. Similar escalating measures may be taken by processor 210 of vehicle 15 to address an emergency condition of passenger 14.

Processor 210 may determine a soothing need or an emergency condition of passenger 14 should one of the following is found based on the monitoring data received from the physiological or user-interface sensors: abnormal breathing, pulse rate, body temperature or blood pressure reading of passenger 14; passenger 14 moving around within vehicle 15 when vehicle 15 is in transit; seatbelt switch of a seat in which passenger 14 is seated being disengaged; window switches or internal door handles being repeatedly touched or manipulated when vehicle 15 is in transit; external door handle being touched or door being opened before vehicle 15 arrives at the destination.

In some embodiments, vehicle 15 may be equipped with one or more impact sensors (e.g., accelerometers) and/or one or more air bags (e.g., air bag 230 of FIG. 2). The impact sensors and the air bags may be triggered or launched if vehicle 15 experiences a collision on the body of vehicle 15. A collision may be categorized as "minor collision" if none of the air bags is launched, whereas a collision may be categorized as "major collision" if at least one of the air bags is launched. That is, the impact sensors may be triggered when vehicle 15 experiences a minor collision, whereas one or more of the airbags may be launched when vehicle 15 experiences a major collision. In an event that vehicle 15 experiences a minor collision, processor 210 of vehicle 15 may, in addition to taking soothing measures as described above, contact or otherwise notify guardian 11 and dispatch center 194 about the minor collision of vehicle 15. As the minor collision may occur when vehicle 15 is in the middle of the predetermined route where traffic may be busy, processor 210 may also, for the safety of passenger 14, lock passenger doors of vehicle 15 through a body control module (BCM) of vehicle 15 to prevent passenger 14 from leaving the vehicle. In an event that vehicle 15 experiences a major collision, processor 210 of vehicle 15 may immediately notify guardian 11 and dispatch center 194 about the major collision of vehicle 15. Furthermore, processor 210 may unlock passenger doors of vehicle 15 through the BCM so as not to hinder passenger 14 from escaping from vehicle 15 in the event of a major collision.

In some embodiments, vehicle 15 may be equipped with a one-touch mechanism (such as a large button labeled "emergency contact") via which passenger 14 may contact at least guardian 11, dispatch center 194, or both, by engaging the mechanism with a simple touch (e.g., pressing down the large button).

Figure 3:
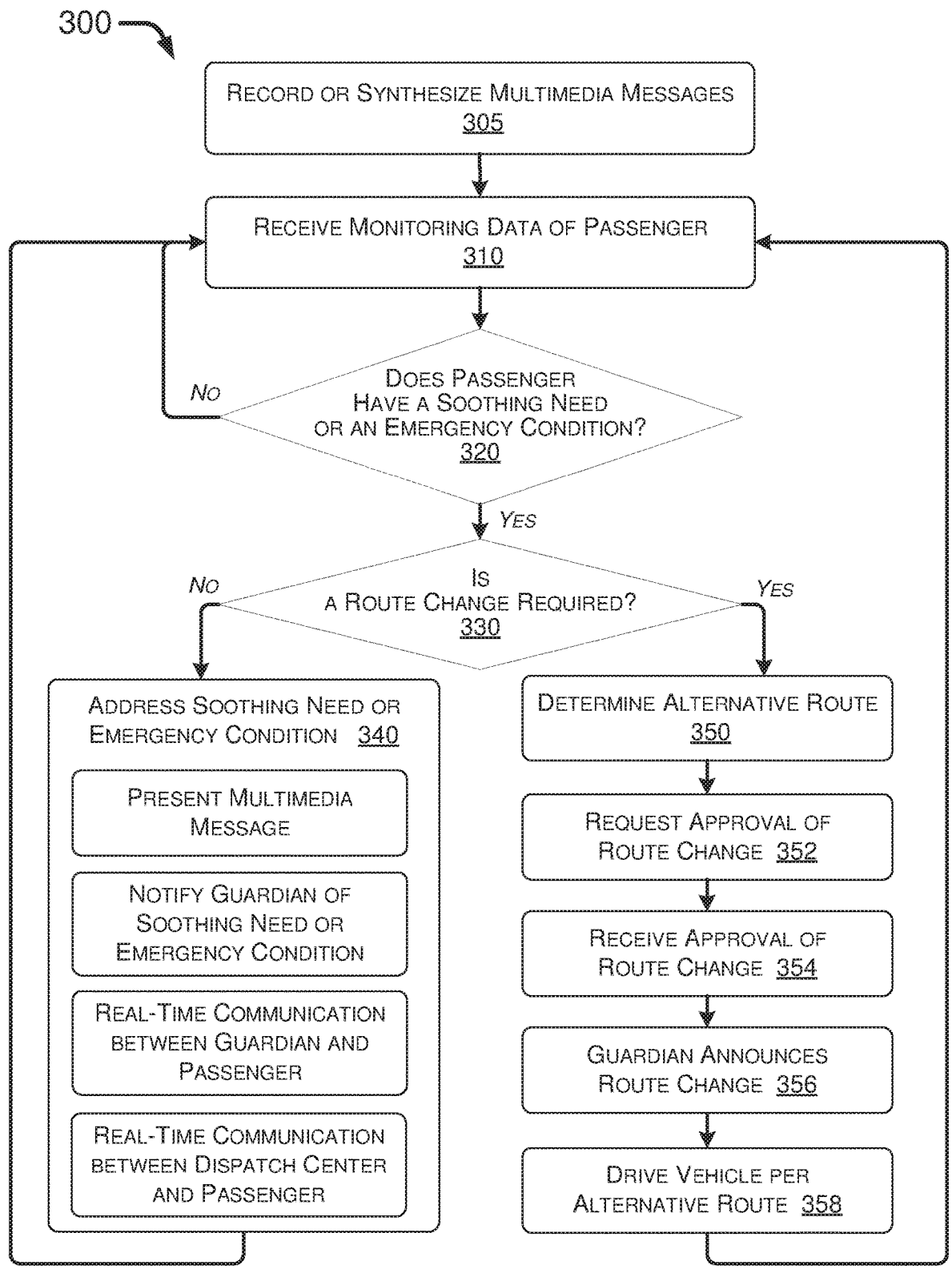
FIG. 3 is a flowchart depicting an example process in accordance with an embodiment of the present disclosure.

FIG. 3 illustrates a flowchart depicting an example process 300 in accordance with an embodiment of the present disclosure. In particular, process 300 shows how a processor of a transportation vehicle may address a soothing need of a passenger of the vehicle, as well as initiating a route change of the vehicle. Process 300 may include one or more operations, actions, or functions shown as blocks such as 305, 310, 320, 330, 340, 350, 352, 354, 356 and 358 of FIG. 3. Although illustrated as discrete blocks, various blocks of process 300 may be divided into additional blocks, combined into fewer blocks, or eliminated, depending on the desired implementation. Process 300 may begin at block 305.

At 305, process 300 may involve the processor (e.g., processor 210 of FIG. 2) of the transportation vehicle (e.g., vehicle 15 of FIG. 1) recording or synthesizing multimedia messages that may be presented to the passenger (e.g., passenger 14 of FIG. 1) to address the soothing need of the passenger. In some embodiments, the multimedia messages may be recorded by a guardian of the passenger (e.g., guardian 11 of FIG. 1). In some embodiments, the multimedia messages may be synthesized or otherwise generated by the processor using audio-synthesis and/or video synthesis techniques, as described above. Process 300 may proceed from 305 to 310.

At 310, process 300 may involve the processor receiving monitoring data relevant to the passenger as the passenger is transported by the vehicle. The monitoring data may be generated or otherwise collected by a plurality of sensors (e.g., the physiological sensors and/or user-interface sensors of vehicle 15). Process 300 may proceed from 310 to 320.

At 320, process 300 may involve the processor determining a soothing need or an emergency condition of the passenger (e.g., the various soothing needs and emergency conditions described above). The processor may determine that the soothing need or the emergency condition exists based on the monitoring data received at block 310. In an event that the processor determines that the passenger does not currently have a soothing need or an emergency condition, process 300 may return from 320 to 310. In an event that the processor determines that the passenger does indeed have a soothing need or an emergency condition, process 300 may proceed from 320 to 330.

At 330, process 300 may involve the processor determining whether a route change (e.g., the route change from predetermined route A-B-C-D-E-F-G to alternative route A-B-C-H of FIG. 1) is required to transport the passenger via an alternative route. The alternative route may lead to the same destination as the predetermined route, or may lead to a different destination (i.e., the alternative destination 193 of FIG. 1). The processor may determine whether a route change is required based on the soothing need or the emergency condition as determined at block 320. In an event that the processor determines a route change is not required, process 300 may proceed from 330 to 340. In an event that the processor determines a route change is required, process 300 may proceed from 330 to 350.

At 340, process 300 may involve the processor addressing the soothing need by one or more of a plurality of soothing measures in an escalating manner, as described above. For example, process 300 may involve the processor presenting a multimedia message (e.g., a multimedia message as described above) that is specific to the passenger and relevant to the soothing need of the passenger. If the soothing need persists, process 300 may, additionally, involve the processor notifying a guardian of the passenger (e.g., guardian 11 of passenger 14 as shown in FIG. 1) about the soothing need. If the soothing need still persists, process 300 may further involve the processor establishing a real-time communication between the guardian and the passenger, as described above. If the soothing need still persists, process 300 may further involve the processor establishing a real-time communication between a dispatch center (e.g., dispatch center 194 of FIG. 1) and the passenger, as described above. Process 300 may proceed from 340 to 310.

At 350, process 300 may involve the processor determining the alternative route (e.g., alternative route A-B-C-H of FIG. 1). The processor may determine the alternative route based on a map of an area in a vicinity of the vehicle. The map may be stored in a memory of the vehicle. Process 300 may proceed from 350 to 352.

At 352, process 300 may involve the processor sending a route change request to the guardian. The route change request may request an approval of the route change from the guardian. Process 300 may proceed from 352 to 354.

At 354, process 300 may involve the processor receiving the approval from the guardian. Process 300 may proceed from 354 to 356.

At 356, process 300 may involve the processor establishing a communication link between the vehicle and the guardian. The guardian may announce the route change to the passenger via the communication link. Process 300 may proceed from 354 to 358.

At 358, process 300 may involve the processor drive or otherwise control the vehicle to transport the passenger using the alternative route (e.g., alternative routes route A-B-C-D-E-K-G to destination 192 or alternative route A-B-C-H to alternative destination 193, as shown in FIG. 1). Process 300 may proceed from 358 to 310.

Figure 4:
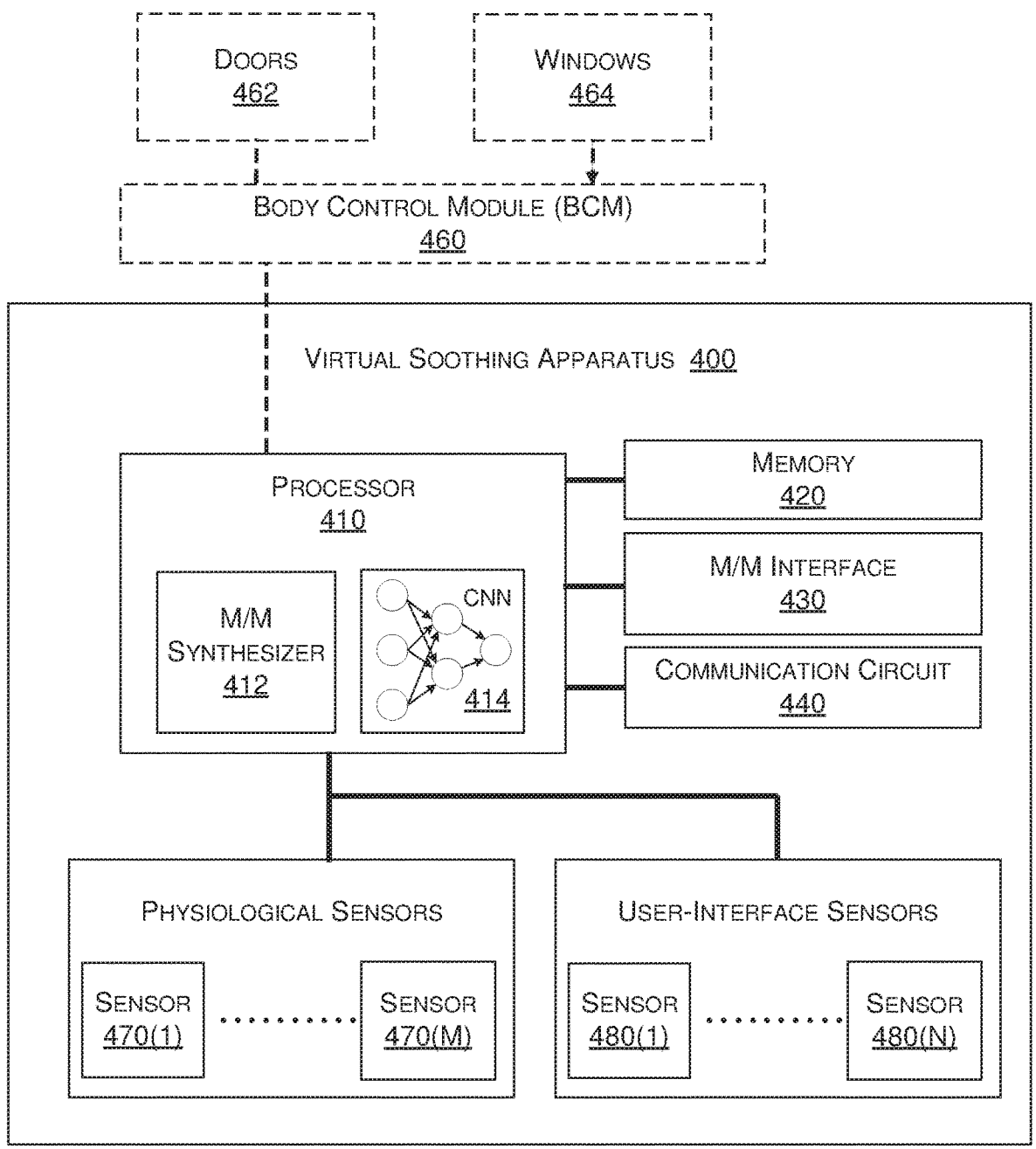
FIG. 4 is a block diagram depicting an example virtual soothing apparatus in accordance with an embodiment of the present disclosure.

FIG. 4 illustrates an example block diagram of a virtual soothing apparatus 400 implementable in a transportation vehicle (e.g., vehicle 15 of FIG. 1 and FIG. 2). Soothing apparatus 400 may include a plurality of physiological sensors 470 (1)-470(M). Physiological sensors 470 (1)-470 (M) may be capable of monitoring vital signs (e.g., a respiration rate, a pulse rate, blood pressure readings and a body temperature) of a passenger (e.g., passenger 14 of FIG. 1) who is being transported by the transportation vehicle. Physiological sensors 470 (1)-470(M) may include one or more of a respiration sensor, a pulse senor, a blood pressure sensor and a thermometer.

Virtual soothing apparatus 400 may also include a plurality of user-interface sensors 480 (1)-480(N). User-interface sensors 480 (1)-480(N) may be capable of monitoring interactions between the passenger and the transportation vehicle. User-interface sensors 480 (1) 480(N) may include one or more of a seat-occupation sensor, a seatbelt-buckling switch, an internal door handle, an external door handle, a window switch, a door-unlock switch, a microphone, a wide-angle video camera and a BLE locator.

Virtual soothing apparatus 400 may also include a computer or a processor 410 (e.g., processor 210 of FIG. 2). Processor 410 may be capable of determining whether a soothing need or an emergency condition of the passenger may exist based on monitoring data generated by one or more of the physiological sensors and the user-interface sensors. In some embodiments, processor 410 may include a multimedia synthesizer 412 (e.g., the multimedia synthesizer of processor 210, as described above). Multimedia synthesizer 412 may be capable of synthesizing a multimedia message, as described in an earlier part of the present application, such that the multimedia message exhibits characteristics that enable the passenger to perceive the multimedia message as being verbally generated by a guardian (e.g., guardian 11 of FIG. 1) with whom the passenger is personally acquainted. In some embodiments, processor 410 may include a CNN 414 (e.g., the CNN of processor 210, as described above). CNN 414 may be capable of interpreting a behavior of the passenger from a video footage captured by a user-interface sensor that comprises a wide-angle video camera. In some embodiments, processor 410 may also be capable of determining a route change based on the emergency condition of the passenger. In some embodiments, processor 410 may further be capable of communicating with BCM 460 of the vehicle to lock or unlock doors 462 and/or windows 464 of the vehicle as needed.

Virtual soothing apparatus 400 may also include a memory 420. Memory 420 may store a plurality of multimedia messages that is useful in addressing the soothing need or the emergency condition of the passenger. Each of the plurality of multimedia messages may include an audio message, a video massage, or both, that are specific to the passenger and relevant to the soothing need or the emergency condition. Characteristics of each of the plurality of multimedia messages may enable the passenger to perceive the multimedia message as being verbally generated by a guardian with whom the passenger is personally acquainted. As described in an earlier part of the present application, some of the plurality of multimedia messages may be verbally generated by the guardian and pre-recorded before the transportation vehicle commences a trip to transport the passenger. In some embodiments, memory 420 may further store a characteristics database and a message content database, as described above, and some of the plurality of multimedia messages may be synthesized or otherwise generated by multimedia synthesizer 412 based on the characteristics database and the message content database stored in memory 420.

Virtual soothing apparatus 400 may further include a multimedia interface 430 (e.g., a speaker and/or a visual display). Multimedia interface 430 may be capable of broadcasting one or more of the plurality of multimedia messages stored in memory 420 to the passenger in an event that the processor determines the soothing need or the emergency condition of the passenger.

In some embodiments, virtual soothing apparatus 400 may also include a communication circuit 440. Communication 440 may be capable of providing a real-time communication link between the passenger and the guardian, as required by at least blocks 340, 352 and 354 of process 300 of FIG. 3. In some embodiments, communication 440 may also be capable of providing a real-time communication link between the passenger and a base station (e.g., dispatch center 194 of FIG. 1). In some embodiments, communication 440 may also be capable of providing a 3-way real-time communication link between the passenger, the guardian and the base station.

In the above disclosure, reference has been made to the accompanying drawings, which form a part hereof, and in which is shown by way of illustration specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, apparatuses, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the present disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including, an in-dash vehicle computer, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the present disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure.

The invention claimed is:

1. A method, comprising:
   receiving, by a processor from a plurality of sensors in a vehicle, first monitoring data relevant to a passenger being transported by the vehicle;
   determining, by the processor based on the first monitoring data, a soothing need or an emergency condition of the passenger;
   presenting, by the processor to the passenger, a multimedia message that addresses the soothing need or the emergency condition;
   receiving, by the processor from the plurality of sensors in the vehicle, second monitoring data relevant to the passenger, wherein the second monitoring data is received subsequent to the first monitoring data being received;
   determining, by the processor based on the second monitoring data, if the soothing need or the emergency condition of the passenger is persisting; and
   escalating, by the processor, at least one soothing measure relevant to the passenger.

2. The method of claim 1, wherein the plurality of sensors comprises one or more of a respiration sensor, a pulse senor, a thermometer, a seat-occupation sensor, a seatbelt-buckling switch, an internal door handle, an external door handle, a window switch, a door-unlock switch, a microphone, a wide-angle video camera and a Bluetooth Low Energy (BLE) locator.

3. The method of claim 1, wherein the multimedia message comprises an audio message, a video massage, or both, specific to the passenger and relevant to the soothing need or the emergency condition, and wherein characteristics of the multimedia message enable the passenger to perceive the multimedia message as being verbally generated by a guardian with whom the passenger is personally acquainted.

4. The method of claim 1, further comprising:
   recording, by the processor, the multimedia message as verbally generated by a guardian of the passenger prior to the determining of the soothing need or the emergency condition, wherein the multimedia message is unique based on characteristics of the guardian and message content that is useful in soothing the passenger.

5. The method of claim 1, further comprising:
   generating, by the processor, the multimedia message using audio-synthesis techniques, video-synthesis techniques, or both.

6. The method of claim 1, wherein the presenting of the multimedia message to the passenger comprises broadcasting the multimedia message through a speaker in the vehicle, displaying the multimedia message on a display in the vehicle, or both.

7. The method of claim 1, further comprising:
   notifying, by the processor, a guardian at a remote location of the soothing need or the emergency condition.

8. The method of claim 7, wherein the notifying the guardian of the soothing need or the emergency condition comprises:
   sending a text message or an email to the guardian, the text message or the email describing the monitoring data and the soothing need or the emergency condition; and
   establishing a one-way communication link from the vehicle to the guardian, the one-way communication link enabling the guardian to monitor the passenger via the one-way communication link in a real-time manner.

9. The method of claim 7, wherein the notifying the guardian of the soothing need or the emergency condition comprises:
   sending a text message or an email to the guardian, the text message or the email describing the monitoring data and the soothing need or the emergency condition; and
   establishing a two-way communication link between the vehicle the guardian, the two-way communication link enabling the guardian and the passenger to communicate to one another via the two-way communication link in a real-time manner over a call.

10. The method of claim 1, wherein the vehicle is equipped with one or more impact sensors, and wherein, in an event that one of the one or more impact sensors is triggered due to a minor collision of the vehicle, the method further comprises:
    locking, by the processor, passenger doors of the vehicle to prevent the passenger from leaving the vehicle; and
    notifying, by the processor, a guardian of the passenger and a dispatch center of the vehicle of the minor collision of the vehicle.

11. The method of claim 1, wherein the vehicle is equipped with one or more air bags, and wherein, in an event that one of the one or more air bags is launched due to a major collision of the vehicle, the method further comprises:
    notifying, by the processor, a guardian of the passenger and a dispatch center of the vehicle of the major collision of the vehicle in response to the event that the one of the one or more air bags is launched.

12. The method of claim 1, wherein the vehicle comprises an autonomous vehicle controlled by the processor to transport the passenger to a destination according to a predetermined route approved by a guardian of the passenger.

13. The method of claim 12, wherein the guardian is not within the vehicle, the method further comprising:
    determining, by the processor based on the emergency condition of the patient, a route change to transport the passenger via an alternative route to an alternative destination;

sending, by the processor to the guardian, a route change request requesting an approval of the route change;

receiving, by the processor from the guardian, the approval; and controlling, by the processor, the vehicle to transport the passenger to the alternative destination via the alternative route in response to the guardian's approval of the route change.

14. The method of claim 13, further comprising: establishing, by the processor, a communication link between the vehicle and the guardian, the communication link enabling the guardian to announce the route change to the passenger via the communication link.

15. An apparatus implementable in a vehicle, comprising:
a plurality of physiological sensors capable of monitoring vital signs of a passenger being transported by the vehicle;
a plurality of user-interface sensors capable of monitoring interactions between the passenger and the vehicle;
a memory capable of storing a plurality of audio-video (multimedia) messages;
a processor capable of determining whether a soothing need or an emergency condition of the passenger exists based on monitoring data generated by one or more of the plurality of physiological sensors and the plurality of user-interface sensors and capable of determining whether the soothing need or the emergency condition of the passenger continues to exist based on the monitoring data generated by the one or more of the plurality of physiological sensors and the plurality of user-interface sensors, wherein the processor is further capable of escalating at least one soothing measure relevant to the passenger if the soothing need or the emergency condition continues to exist; and
a multimedia interface capable of presenting one or more of the plurality of multimedia messages to the passenger in an event that the processor determines that the soothing need or the emergency condition exists.

16. The apparatus of claim 15, wherein:
the plurality of physiological sensors comprises one or more of a respiration sensor, a pulse senor and a thermometer,
the plurality of user-interface sensors comprises one or more of a seat-occupied sensor, a seatbelt-buckled switch, an internal door handle, an external door handle, a window switch, a door-unlock switch, a microphone, a wide-angle video camera and a Bluetooth Low Energy (BLE) locator,
the multimedia interface comprises a speaker, a display, or both,
each of the plurality of multimedia messages comprises an audio message, a video message, or both, that are specific to the passenger and relevant to the soothing need or the emergency condition, wherein the multimedia message is unique based on characteristics of the guardian and message content that is useful in soothing the passenger, and
characteristics of each of the plurality of multimedia messages enable the passenger to perceive the multimedia message as being verbally generated by a guardian with whom the passenger is personally acquainted.

17. The apparatus of claim 16, wherein the processor comprises a multimedia synthesizer capable of synthesizing the multimedia messages such that the multimedia messages exhibit the characteristics.

18. The apparatus of claim 16, wherein each of the plurality of multimedia messages is verbally generated by the guardian and pre-recorded such that the multimedia messages exhibit the characteristics.

19. The apparatus of claim 15, further comprising:
a communication circuit capable of providing a real-time communication link between the passenger and the guardian.

20. The apparatus of claim 15, wherein the processor is further capable of determining a route change based on the emergency condition of the passenger.

* * * * *